US00PP27813P3

(12) United States Plant Patent
Ferguson et al.

(10) Patent No.: US PP27,813 P3
(45) Date of Patent: Mar. 28, 2017

(54) STRAWBERRY PLANT NAMED 'DRISSTRAWFORTYSEVEN'

(50) Latin Name: *Fragaria×ananassa*
Varietal Denomination: DrisStrawFortySeven

(71) Applicant: Driscoll's, Inc., Watsonville, CA (US)

(72) Inventors: Michael D. Ferguson, Moorpark, CA (US); Terrance C. Moran, Naples, FL (US); Josefa Lagunas, Port Hueneme, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 14/545,992

(22) Filed: Jul. 15, 2015

(65) Prior Publication Data

US 2017/0020046 P1 Jan. 19, 2017

(51) Int. Cl.
*A01H 5/08* (2006.01)

(52) U.S. Cl.
USPC ..... Plt./208

(58) Field of Classification Search
USPC ..... Plt./208, 209
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.

(Continued)

OTHER PUBLICATIONS

Kibbe et al., U.S. Appl. No. 14/545,991, filed Jul. 15, 2015 titled "Strawberry Plant Named Drisstrawfortysix".

(Continued)

*Primary Examiner* — Susan McCormick Ewoldt
(74) *Attorney, Agent, or Firm* — Morrison & Foerster LLP

(57) ABSTRACT

A new and distinct variety of strawberry plant named 'DrisStrawFortySeven' particularly characterized by having large, dark red, sweet fruit, a globose—semi-upright plant habit, and resistance to *Tetranychus urticae*, is disclosed.

5 Drawing Sheets

(56) References Cited

U.S. PATENT DOCUMENTS

| | | | |
|---|---|---|---|
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| 2003/0079263 | P1 | 4/2003 | Gilford et al. |
| 2013/0276182 | P1 | 10/2013 | Fear et al. |
| 2016/0270276 | P1 | 9/2016 | Vitten et al. |
| 2016/0302339 | P1 | 10/2016 | Vitten et al. |

OTHER PUBLICATIONS

Kibbe et al., U.S. Appl. No. 14/756,125, filed Aug. 4, 2015, titled "Strawberry Plant Named Drisstrawfortyeight".

Vitten et al, U.S. Appl. No. 14/999,062, filed Mar. 25, 2016 titled "Strawberry Plant Named Drisstrawfifty".

Genus and species: *Fragaria×ananassa.*

Variety denomination: 'DrisStrawFortySeven'.

BACKGROUND OF THE NEW PLANT

The present invention relates to a new and distinct strawberry variety designated 'DrisStrawFortySeven' and botanically known as *Fragaria×ananassa*. This new strawberry variety was discovered in Ventura County, Calif. in January 2009 and originated from a cross between the proprietary female parent '41Q324' (unpatented) and the proprietary male parent 'DrisStrawThirtySeven' (U.S. Plant Pat. No. 25,866). A single plant was selected and asexually propagated via tissue culture and vegetative cuttings in Shasta County, Calif. in 2009.

'DrisStrawFortySeven' underwent further testing in Ventura County, Calif. from 2010-2015. The present invention has been found to retain its distinctive characteristics through successive asexual propagations via stolons and tissue culture.

SUMMARY OF THE INVENTION

The following are the most outstanding and distinguishing characteristics of this new cultivar when grown under normal horticultural practices in Ventura County, Calif.

1. Large, dark red, sweet fruit;
2. Globose—semi-upright plant habit; and
3. Resistant to *Tetranychus urticae.*

DESCRIPTION OF THE PHOTOGRAPHS

The accompanying color photographs show typical specimens of the new variety at various stages of development. The colors shown are as true as can be reasonably obtained by conventional photographic procedures. The photographs were taken from five-month-old plants.

DESCRIPTION OF THE NEW VARIETY

Figure 1A:
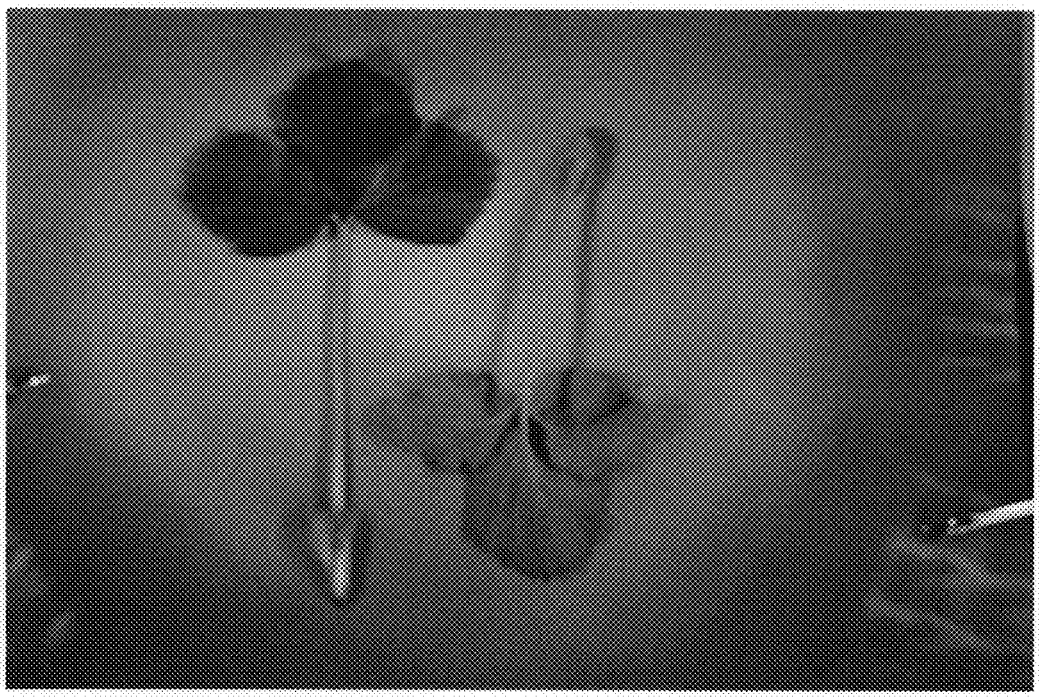
FIG. 1A shows upper and lower surfaces of the leaves of the plant with three leaflets.
Figure 1B:
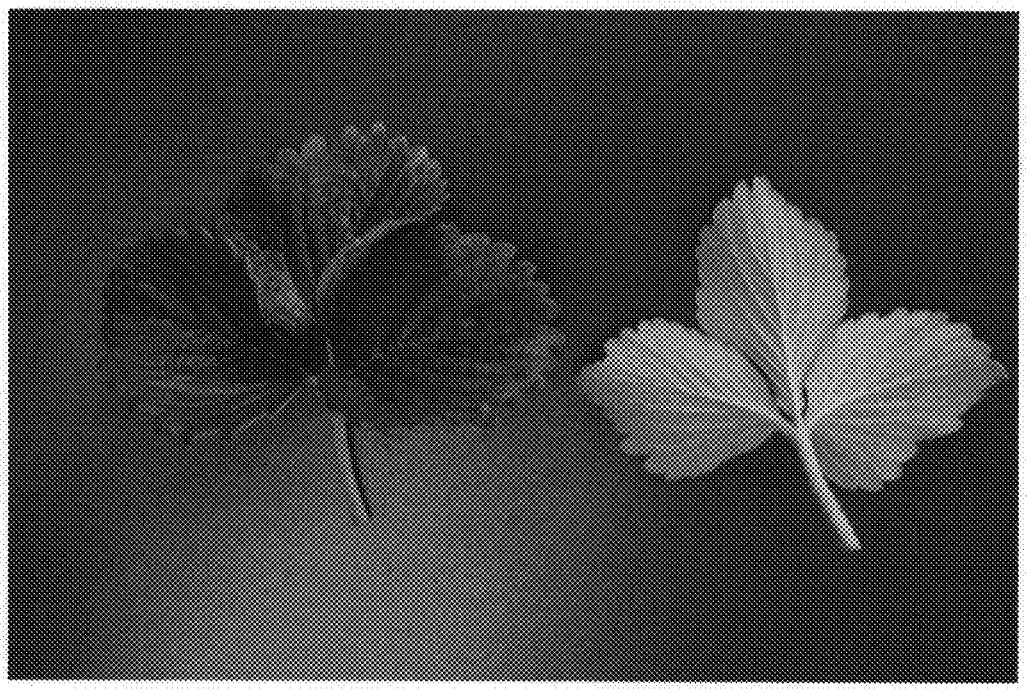
FIG. 1B shows upper and lower surfaces of the leaves of the plant with three leaflets.
Figure 2:
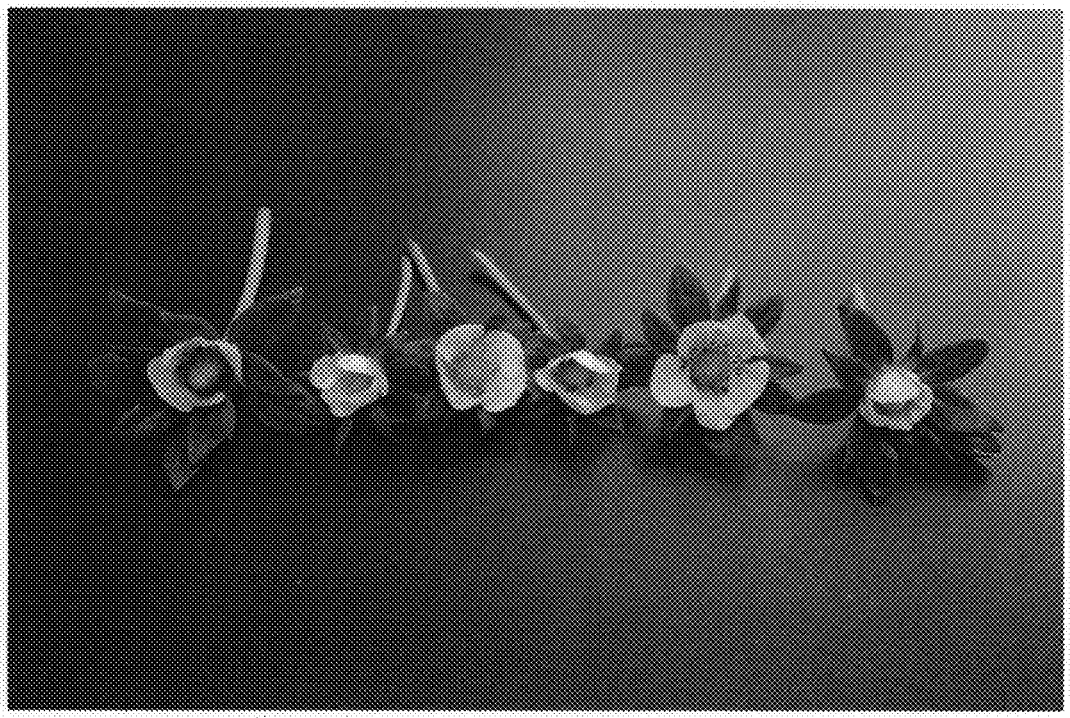
FIG. 2 shows flowers of strawberry plant variety 'DrisStrawFortySeven'.
Figure 3A:
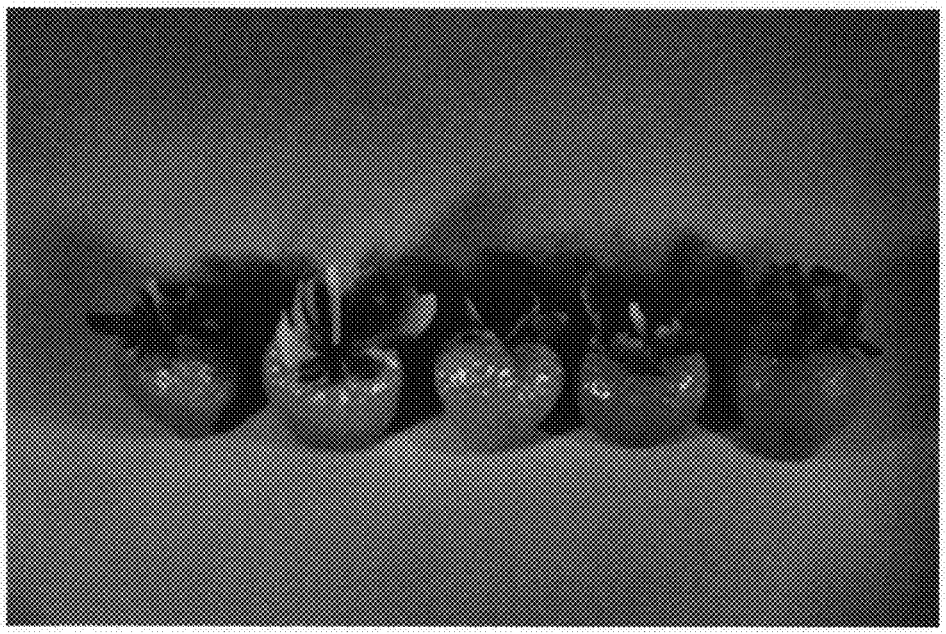
FIG. 3A shows the whole fruit.
Figure 3B:
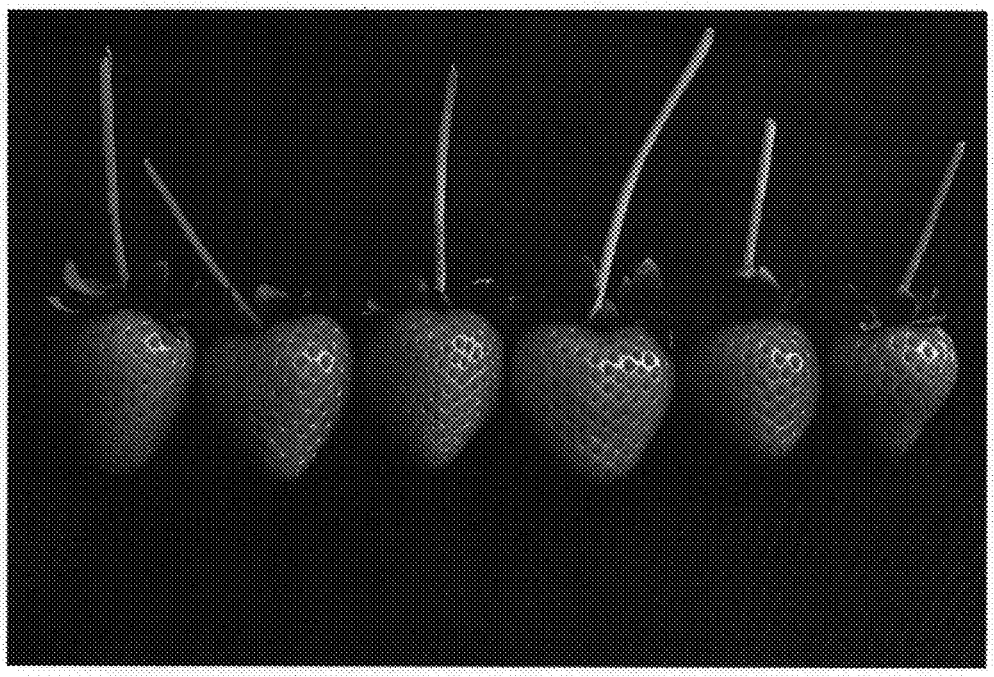
FIG. 3B shows the whole fruit with stems.
Figure 4A:
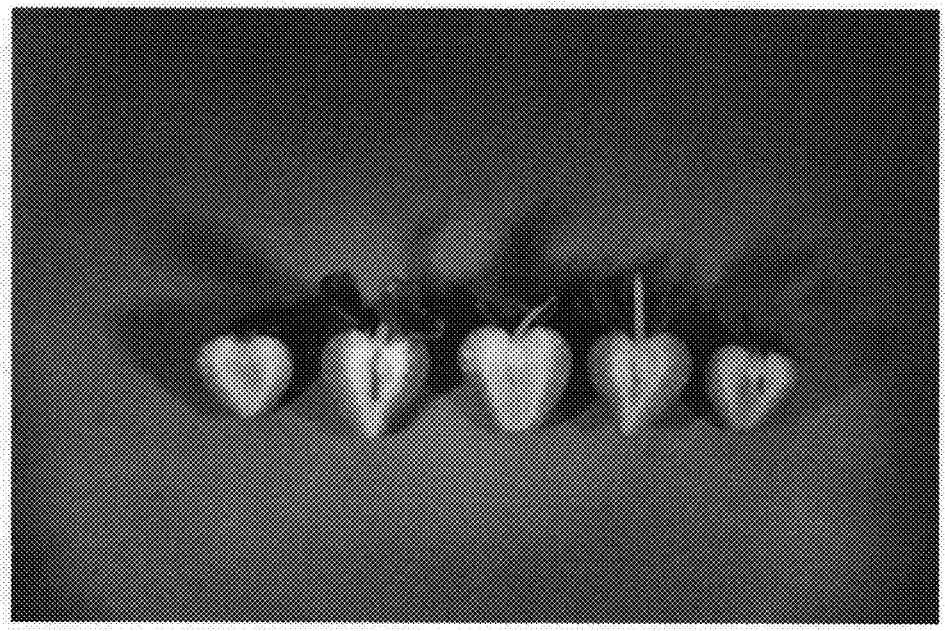
FIG. 4A shows the fruit in longitudinal cross-section.
Figure 4B:
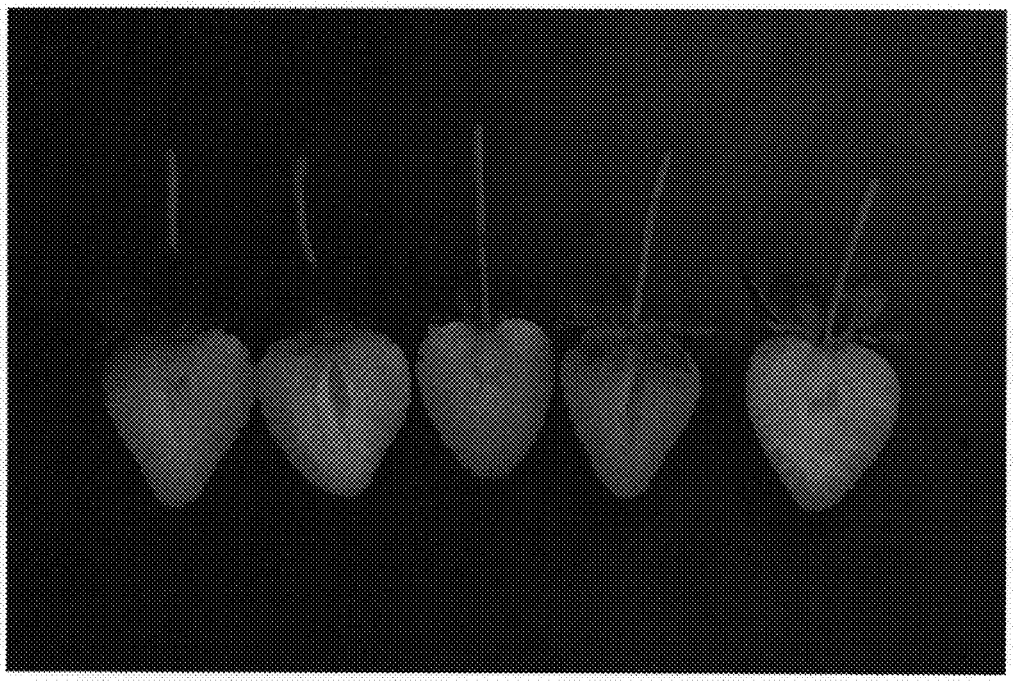
FIG. 4B shows the fruit in longitudinal cross-section with stems.
Figure 5:
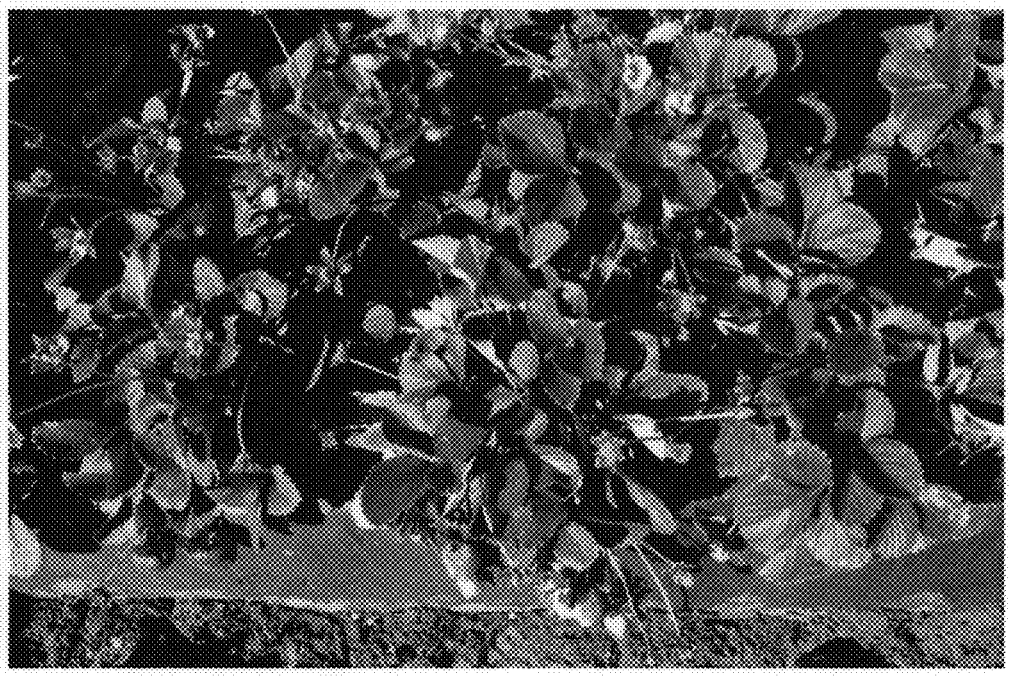
FIG. 5 shows the entire plant habit.

The following detailed descriptions set forth the distinctive characteristics of 'DrisStrawFortySeven'. The data which define these characteristics is based on observations taken in Ventura County, Calif. from 2010 to 2015. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortySeven' has not been observed under all possible environmental conditions. The botanical description of 'DrisStrawFortySeven' was taken from five-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*

*Common name.*—Strawberry.

*Denomination.*—'DrisStrawFortySeven'.

Parentage:

*Female parent.*—The proprietary variety '41Q324' (unpatented).

*Male parent.*—The proprietary variety 'DrisStrawThirtySeven' (U.S. Plant Pat. No. 25,866).

Plant:
*Height.*—20.5 cm.
*Diameter.*—34.8 cm.
*Number of crowns/plant.*—4.
*Habit.*—Globose — semi-upright.
*Density of individual plant.*—Medium.
*Vigor* (*health and hardiness of plant*).—Medium.

Terminal leaflets:
*Size.*—Medium. Length: 7.2 cm. Width: 6.5 cm. Length/width ratio: 1.1 (Longer than broad).
*Number of teeth/terminal leaflet.*—23.
*Shape of teeth.*—Rounded — crenate.
*Color.*—Upper surface: RHS N137A (Dark green). Lower surface: RHS 147C (Medium yellow-green).
*Shape in cross section.*—Concave.
*Blistering.*—Weak.
*Glossiness.*—Medium.
*Number of leaflets.*—Three only.
*Shape.*—Orbicular.
*Base shape.*—Rounded.
*Apex descriptor.*—Rounded.
*Margin.*—Crenate.
*Margin profile.*—Both revolute (margins rolled backwards) and flat (level with the leaflet blade).
*Variegation.*—Absent.

Petiole:
*Length.*—Medium; 12.2 cm.
*Diameter.*—4.32 mm.
*Pubescence.*—Dense.
*Pose of hairs.*—Slightly upwards.
*Color.*—RHS 144D (Light yellow-green).
*Bract frequency.*—0.

Petiolule:
*Length.*—7.20 mm.
*Diameter.*—2.07 mm.
*Color.*—RHS 144D (Light yellow-green).

Stipule:
*Length.*—3.9 cm.
*Width.*—10.17 mm.
*Pubescence.*—Dense.
*Stipule anthocyanin coloration.*—Medium; RHS 63D (Light red-purple).

Inflorescence:
*Position relative to foliage.*—Above.
*Number of flowers per plant.*—Many; 18.70.
*Time of flowering* (*50% of plants at first flower*).—Early; late November-early January.
*Flower size.*—Medium.
*Flower diameter.*—23.10 mm.
*Petals.*—Shape: Orbicular. Apex: Rounded. Base: Concavo-convex. Margin: Entire. Spacing: Overlapping. Length: 16.23 mm. Width: 16.70 mm. Length/width ratio: 1.0 (Broader than long). Petal number per flower: 6. Color (upper surface): RHS NN155B (White).
*Calyx.*—Diameter: 35.13 mm. Diameter relative to corolla: Larger. Inner calyx diameter relative to outer: Both smaller and same size. Insertion of calyx: Level. Pose of calyx segments: Both spreading — outwards and reflexed — upwards. Size of calyx in relation to fruit: Slightly larger. Adherence of calyx: Strong.
*Sepal.*—Shape: Elliptical. Apex: Convex. Margin: Entire. Length: 38.11 mm. Width: 9.32 mm. Sepal number: 12.
*Receptacle color.*—RHS 151C (Light green-yellow).
*Stamen.*—Present. Anther color: RHS 163C (Greyed orange).
*Pedicel.*—Attitude of hairs: Upwards.

Fruiting truss:
*Length.*—Long; 23.8 cm.
*Diameter at base of truss.*—4.71 mm.
*Number of berries per fruiting truss.*—2.
*Attitude at first picking.*—Semi-erect.
*Color at base of truss.*—RHS 144C (Light yellow-green).

Fruit:
*Relative fruit size.*—Large.
*Length.*—43.15 mm.
*Width.*—44.16 mm.
*Length/width ratio.*—1.0 (Broader than long).
*Fruit hollow length.*—22.49 mm.
*Fruit hollow width.*—21.29 mm.
*Fruit hollow length/width ratio.*—1.1 (Longer than broad).
*Fruit hollow center* (*cavity*).—Small.
*Fruit weight.*—32.9 g.
*Predominant fruit shape.*—Conical.
*Difference in shape between primary and secondary fruits.*—Moderate.
*Evenness of fruit surface.*—Slightly uneven.
*Fruit skin color.*—RHS 46A (Dark red).
*Evenness of fruit color.*—Even or very slightly uneven.
*Fruit glossiness.*—Medium.
*Achenes.*—Insertion of achenes: Level with surface. Coloration (sunward side of berry): RHS 181C (Dark red). Coloration (shaded side of berry): RHS 144D (Light yellow-green). Number per berry: 199. Weight (weight of achenes divided by total # seed): 0.153 g. Width of band without achenes: Narrow.
*Firmness of flesh* (*when fully ripe*).—Firm.
*Color of flesh* (*excluding core*).—RHS 43A (Medium red) and 69D (Light red-purple).
*Color of core.*—RHS 38A (Light red).
*Evenness of flesh color.*—Slightly uneven.
*Distribution of flesh color.*—Marginal and central.
*Sweetness.*—Strong.
*Acidity.*—Weak.
*Texture when tasted.*—Coarse.
*Type of bearing.*—Not everbearing — not remontant.
*Harvest interval.*—Mid-December-mid-January.
*Harvest maturity.*—Mid-season.
*Production.*—1058 grams per plant.

Disease and pest resistance:
*Tetranychus urticae.*—Resistant.
*Lygus hesperus* (*Lygus* bug).—Moderately susceptible.
*Botrytis fruit rot.*—Moderately susceptible.
*Powdery mildew.*—Moderately resistant.

Stress resistance:
*High temperatures.*—Moderately resistant.
*Wind.*—Moderately resistant.
*High pH.*—Moderately resistant.
*High soil salt levels.*—Moderately resistant.
*Water logging.*—Moderately resistant.

COMPARISON WITH PARENTAL AND COMMERCIAL VARIETIES

When 'DrisStrawFortySeven' is compared to the female parent '41Q324' (unpatented), 'DrisStrawFortySeven' is firmer with a more conic shape and better fruit appearance than '41Q324'.

When 'DrisStrawFortySeven' is compared to the male parent 'DrisStrawThirtySeven' (U.S. Plant Pat. No. 25,866), 'DrisStrawFortySeven' is less firm with lower yields and earlier production than 'DrisStrawThirtySeven'.

'DrisStrawFortySeven' differs from the commercial variety 'DrisStrawTwentySeven' (U.S. Plant Pat. No. 23,400), in that 'DrisStrawFortySeven' has a globose—semi-upright plant habit and four crown per plant, whereas 'DrisStrawTwentySeven' has a flat globose plant habit and three crowns per plant. Additionally, 'DrisStrawFortySeven' has large, medium glossy fruit, whereas 'DrisStrawTwentySeven' has very large, strongly glossy fruit.

We claim:

1. A new and distinct variety of strawberry plant named 'DrisStrawFortySeven', substantially as illustrated and described herein.

* * * * *